United States Patent [19]

Lotman

[11] Patent Number: 4,873,710
[45] Date of Patent: Oct. 10, 1989

[54] PATIENT SUPPORT

[76] Inventor: David B. Lotman, 13175 Sand Grouse Ct., Palm Beach Gardens, Fla. 33418

[21] Appl. No.: 144,469

[22] Filed: Jan. 15, 1988

[51] Int. Cl.⁴ .............. A61G 7/10; A47C 27/10; A61B 6/04
[52] U.S. Cl. ...................... 378/177; 378/185; 378/209; 5/81 R; 5/453; 5/455; 5/456
[58] Field of Search .......... 5/81 R, 81 B, 61, 455, 5/453, 456, 446, 434, 441; 378/177, 209, 180; 269/322, 328

[56] References Cited

U.S. PATENT DOCUMENTS

| | | | |
|---|---|---|---|
| 595,734 | 12/1897 | Rand et al. | 5/455 |
| 2,245,909 | 6/1941 | Enfiajian | 5/455 |
| 3,535,719 | 10/1970 | Murcott | 5/424 |
| 3,795,021 | 3/1974 | Moniot | 5/441 |
| 3,935,604 | 2/1976 | Collins | 5/61 |
| 4,024,861 | 5/1977 | Vincent | 5/82 R |
| 4,156,145 | 5/1979 | Weatherholt | 378/177 |
| 4,175,297 | 11/1979 | Robbins et al. | 5/447 |
| 4,190,286 | 2/1980 | Bentley | 5/455 |
| 4,617,690 | 10/1986 | Grebe | 5/453 |
| 4,745,647 | 5/1988 | Goodwin | 5/453 |

Primary Examiner—Alexander Grosz
Attorney, Agent, or Firm—Steele, Gould & Fried

[57] ABSTRACT

A patient support includes a support surface and structure positioned about the support surface for lifting selected portions of the patient's body from the support surface so as to permit the insertion of an x-ray cassette beneath the selected portion of the patient's body. The structure for lifting preferably includes a plurality of inflatable runners. Structure for placing the inflatable runners in fluid connection with fluid supply means is provided such that the runners can be inflated. The runners are spaced apart from one another and adapted when inflated to lift an adjacent portion of the patient so as to permit the insertion of an x-ray cassette between adjacent runners and beneath the patient.

32 Claims, 2 Drawing Sheets

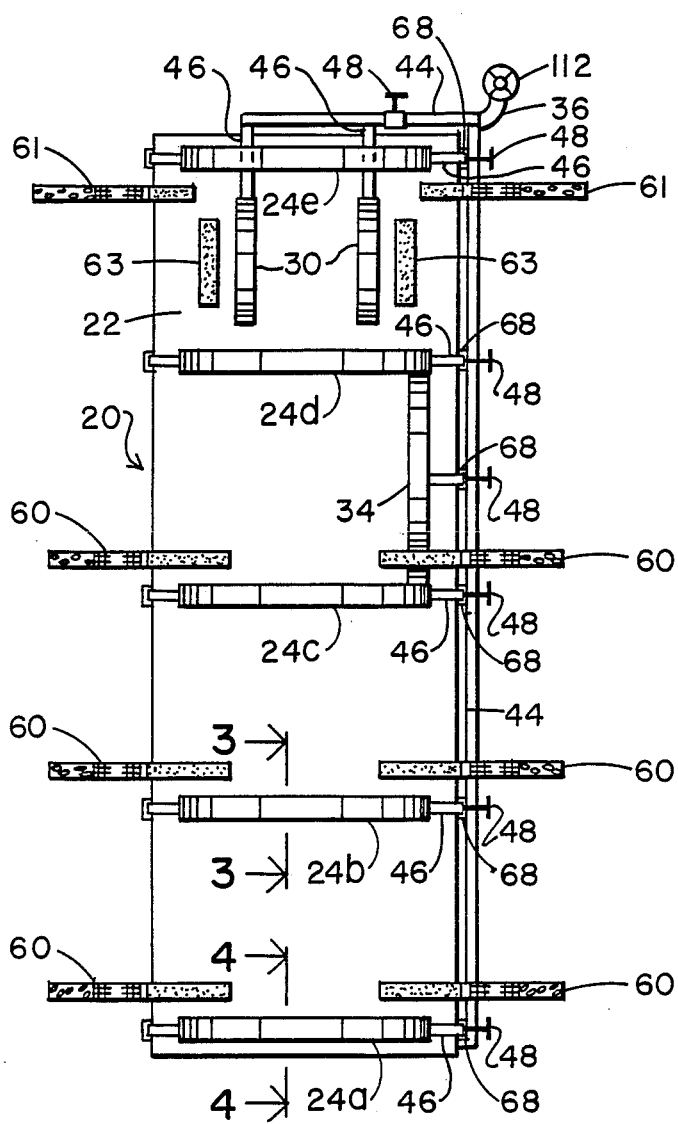
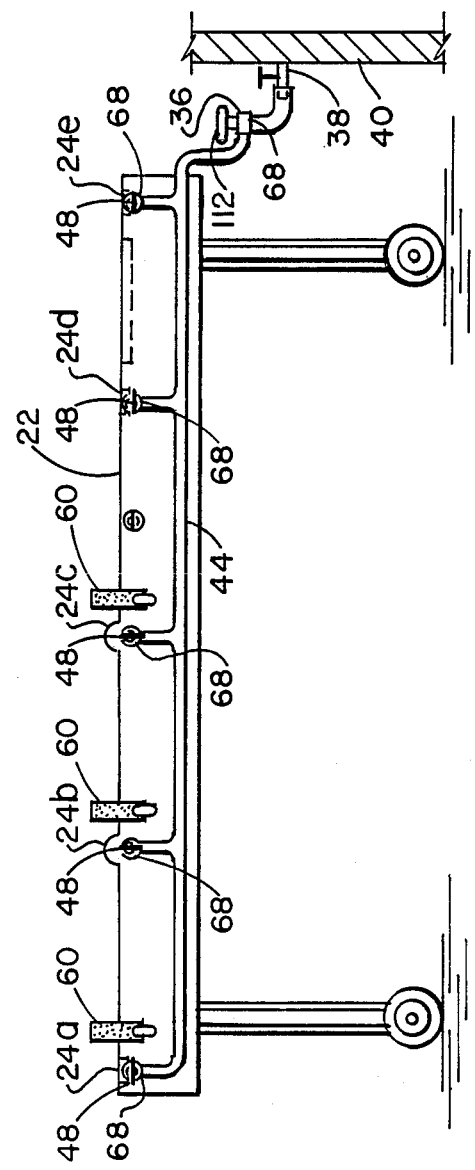
FIG. 1
FIG. 2
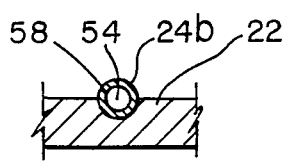
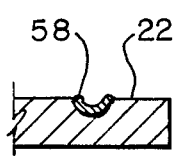
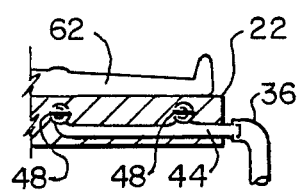
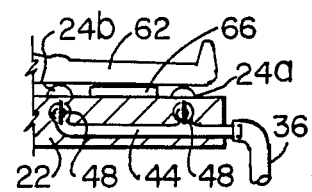
FIG. 3　　FIG. 4　　FIG. 5　　FIG. 6

PATIENT SUPPORT

BACKGROUND OF THE INVENTION

1. Field of the Invention

This invention relates generally to medical equipment, and more particularly to patient supports for use in medical facilities.

2. Description of the Prior Art

Bedridden hospital patients must sometimes be x-rayed and it is necessary to place an x-ray cassette beneath the body part that is to be x-rayed. This requires attendants to lift the patient's entire body, or at least the part of the body to be x-rayed, from the patient support. Some patients, particularly those in trauma situations, should not be moved or, if movement is absolutely necessary, must be moved with great care to avoid further injury and discomfort to the patient. It is difficult to manually move a patient without some jarring and there is at present no convenient method or means for x-raying a patient without disturbing the patient.

SUMMARY OF THE INVENTION

It is an object of the invention to provide a patient support which will permit the insertion of an x-ray cassette beneath the patient.

It is another object of the invention to provide a patient support which will not disturb the patient.

It is another object of the invention to provide a patient support which will permit the insertion of an x-ray cassette under virtually any portion of the patient's body.

These and other objects are accomplished by a patient support for a patient comprising a support surface with means positioned about the support surface for lifting selected portions of the patient's body from the support surface so as to permit the insertion of an x-ray cassette beneath the selected portion of the patient's body. The means for lifting preferably comprises a plurality of inflatable runners. Means for placing the inflatable runners in fluid connection with fluid supply means are provided so that the runners can be inflated. The runners are spaced apart from one another and adapted when inflated to lift an adjacent portion of the patient so as to permit the insertion of an x-ray cassette beneath the patient and between adjacent runners.

The runners preferably are substantially parallel and laterally aligned on the patient support so as to be substantially parallel with the axis of the shoulders of the patient. The x-ray cassette can thereby be inserted from along the side of the patient and positioned between adjacent runners at a plurality of locations relative to the body of the patient.

The means for placing the inflatable runners in fluid connection with the fluid supply means preferably comprises a manifold which forms a passage for fluid between the fluid supply means and the interior spaces of the hollow runners. Valves are preferably located in lines connecting the manifold to the various runners. The runners are thereby selectively inflatable depending on an open or closed condition of the valves and it is possible to move only the portion of the patient's body that will be x-rayed.

The valves are preferably three position valves providing a closed condition, an inflating condition, and an exhaust condition. The exhaust condition permits the fluid to escape and thus deflate the runner. The fluid can be permitted to escape to the atmosphere if it is a gas and is not harmful, or can be returned to a fluid storage tank through suitable conduit means.

Electric control can be provided so that the patient support of the invention can be operated without the necessity of manually turning valves. The valves can be made operable by electric solenoids. The electric solenoids are preferably operable to position the valves in either of the three positions. A control panel can be provided so that the operator does not have to walk around the table to activate the solenoids.

The runners preferably are fixed directly to the support surface. The runners can be made from any suitable material, but preferably are formed from a flexible material that collapses when deflated to restore as plane a surface as possible for the comfort of the patient. The runners can be fixed in concave depressions formed in the support surface so that the accumulated runner material, when deflated, falls within the cavity and does not cause the patient discomfort.

The runners preferably are constructed so as to lift the adjacent portion of the patient's body at least two inches to permit proper insertion and removal of the x-ray cassette.

The number of runners and their position on the support surface can be varied. It is preferable to provide a plurality of lateral runners dispersed along the longitudinal length of the patient support so that virtually any portion of the patient's body can be x-rayed. The lateral runners must be separated by a sufficient distance to permit the insertion of an x-ray cassette between adjacent runners. A typical x-ray cassette might measure 10×12 inches, so it is desirable that the spacing between runners be at least 10 inches. One lateral runner is preferably positioned on the patient support so as to lift the foot of the patient when the runner is inflated. Other runners preferably are positioned on the patient support so as to substantially lift the knee, the pelvis, the upper chest, and the head of the patient. At least two substantially parallel head and neck restraint runners can be positioned substantially perpendicular to the axis of the shoulders and spaced apart so as to restrain the head of the patient therebetween when the restraint runners are inflated.

The support surface preferably is a mattress or other padded support which increases the patient's comfort. It is within the scope of the invention, however, to use a rigid support.

Other configurations of the runners are possible. At least one longitudinally aligned runner can be placed between two lateral runners substantially at one lateral side of the patient support so that a substantially U-shaped runner is formed. This configuration can more effectively lift the patient.

The fluid supply means can be the oxygen supply into the emergency room or operating room. Where additional pressure is necessary, a separate fluid supply can be provided. Gases are preferred but it is within the scope of the invention to use not only gas but also liquids such as water or oil.

Restraining straps to restrain the patient are preferably affixed to the patient support and can conveniently be positioned between the runners. The restraining straps preferably comprise hook and loop fasteners such as Velcro for fast and convenient fastening.

BRIEF DESCRIPTION OF THE DRAWINGS

There is shown in the drawings embodiments which are presently preferred, it being understood, that the invention is not limited to the precise arrangements and instrumentalities shown, wherein:

FIG. 1 is a plan view of a patient support according to the invention.

FIG. 2 is a side elevation.

FIG. 3 is a cross-section taken along line 3-3 in FIG. 1.

FIG. 4 is a cross-section taken along line 4-4 in FIG. 1.

FIG. 5 is a side elevation showing a patient on a patient support according to the invention with runners in the deflated state.

FIG. 6 is a side elevation showing a patient on a patient support according to the invention with runners inflated and an x-ray cassette in position.

DETAILED DESCRIPTION OF THE PREFERRED EMBODIMENTS

Figure 7:
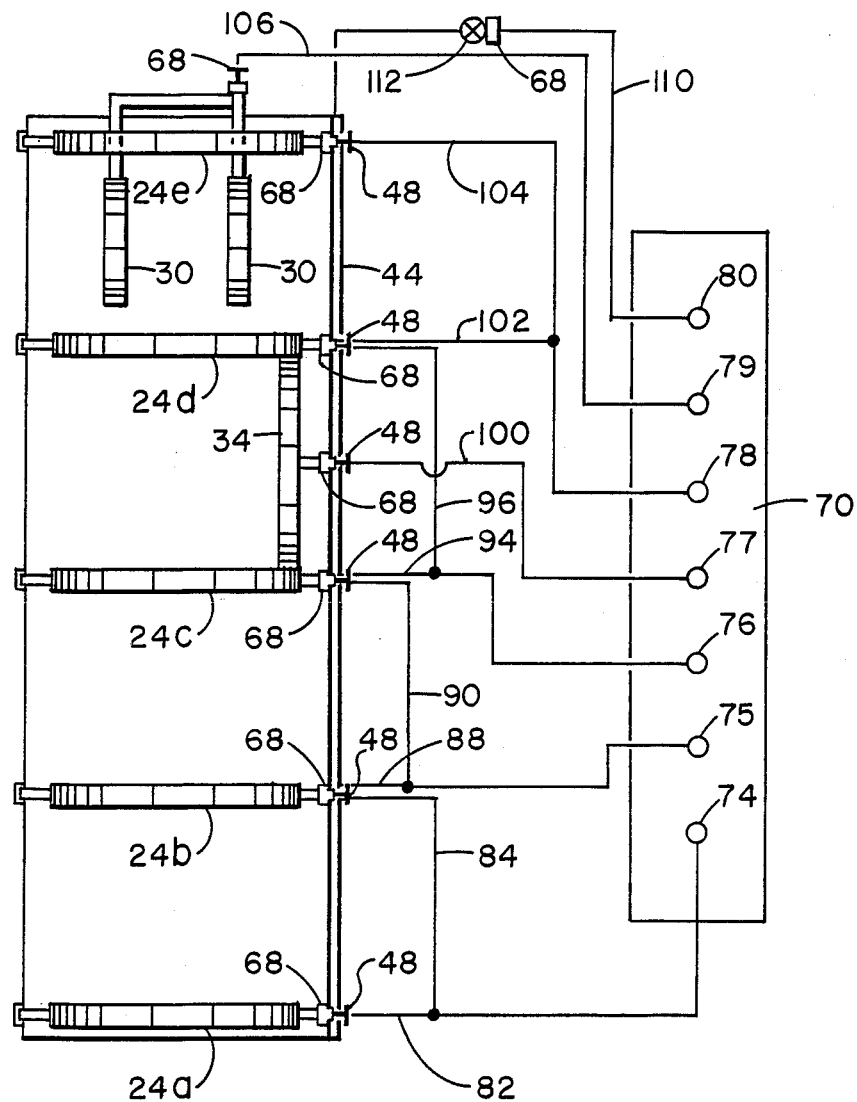
FIG. 7 is a schematic diagram showing electric control of the invention.

Referring to FIGS. 1-4, there is shown a patient support 20 according to the invention. The patient support comprises a support surface 22 which can be formed similarly to traditional hospital mattresses and, thus, can be constructed of foam or the like. A number of inflatable runners are provided on the surface of the patient support 22. These runners are spaced apart from one another and adapted, when inflated, to lift an adjacent portion of the patient so as to permit the insertion of an x-ray cassette beneath the patient's body. A number of laterally aligned runners 24a-e are preferably dispersed about the longitudinal length of the patient support 22. The number and position of the runners can be varied, but it is preferred to provide five lateral runners 24a-e as shown. The lateral runners 24a-e are spaced apart sufficiently to permit the insertion therebetween of a standard x-ray cassette. These cassettes can vary in size, but commonly are 10×12 inches. It then is preferable for a standard patient support to separate the lateral runners 24a-e by at least 10 inches.

A lateral runner 24a can be positioned at the foot area of the patient support 22 to substantially lift the foot of the patient. Another runner 24b can be positioned to lift the knee area of the patient. A third runner 24c can be positioned to lift the pelvic area of the patient. Another lateral runner 24d can be positioned to lift the upper chest area of the patient. A fifth lateral runner 24e can be positioned to lift the head of the patient. Current emergency room supports are approximately 24×72 inches in dimension. The first runner 24a is preferably one inch from the foot of the patient support. The fifth runner 24e is preferably four inches from the head of the patient support. Remaining runners are spaced apart from one another by 15 inches.

It is also desirable to provide at least two head restraint runners 30 which can be substantially parallel and substantially perpendicular to the axis of the shoulders and spaced apart so as to restrain the head of the patient therebetween when the head restraint runners 30 are inflated. Longitudinal runners can also be provided between the lateral runners and at a lateral side of the patient support 22. A longitudinal runner 34 between the lateral runners 24c and 24d forms a substantially U-shaped lifting structure with the lateral runners to give good support to the patient while permitting placement and removal of the x-ray cassette.

The runners are inflated by a supply of suitable fluid. The fluid can be a liquid such as water or oil, but preferably is a gas. The gas can be provided from a fluid supply means adapted specifically for this purpose, but preferably means are provided for connecting the runners to the oxygen supply lines in existence in most emergency and operating rooms. This connection can be an elastomeric hose 36 which fits onto an oxygen outlet such as the wall-mounted nozzle 38 which extends outwardly from the wall 40. The connection hose 36 preferably connects to a manifold 44 which supplies the gas to each of the runners. Connection lines 46 place the individual runners in fluid connection with the manifold 44. The manifold 44 can be conveniently fixed to a side of the patient support 22 by suitable fastening means or straps.

It is preferable to provide means for selectively inflating the runners so that only the body part that must be x-rayed is lifted. This can be accomplished by providing valves 48 in the fluid flow lines to the individual runners. A preferable position for the valves 48 is in the connection lines 46 upstream from the runners or as shown at the juncture of the connection lines 46 with the manifold 44. The valves 48 can be of suitable construction known in the art for this purpose. The valves 48 can be of any suitable construction, but preferably are three position valves to provide a closed condition, an open and thus inflation condition, and an exhaust condition. The exhaust condition permits the fluid to escape and thus deflate the runner. The fluid can be permitted to escape to the atmosphere if it is a harmless gas or it can be returned to a fluid storage tank by the incorporation of suitable conduit structure.

The runners are preferably formed from fluid-tight flexible tubes that can be inflated by introducing the fluid into the hollow core 54 of the runners (FIG. 3). It is desirable to fix the runners in a concave seat 58 formed in the support surface 22. The flexible tube material will gather in the depression when the fluid pressure is removed instead of gathering on the surface of the patient support, so that the presence of the material will not cause the patient discomfort (FIG. 4).

Additional structure useful with trauma beds can be combined with the patient support of the invention. Restraining straps 60 can be secured to the patient support in positions suitable for restraining the arms and legs of the patient. The restraining straps can comprise hook and loop fastening structure such as Velcro for fast and convenient fastening. Head restraint straps 61 can be provided with hook and loop fasteners such as Velcro and are positioned on the support surface 22 so as to cross over and secure the forehead of the patient. Fastening means such as loop strips 63 can be provided on the support surface 22 to engage cooperating fastening structure such as hook strips attached to structure adapted to hold syringes, scissors, tape or the like.

Operation of the patient support is shown in FIGS. 5-6. The leg 62 of the patient rests directly on the patient support 22 (FIG. 5). It is necessary to insert an x-ray cassette beneath the leg 62 in order to x-ray the leg 62. Normally this would require manually moving the patient which often results in bumps and jars that can cause the patient great discomfort or additional injury. In the present invention, fluid is supplied through the supply line 36 which can be connected to the oxygen supply in the emergency room. The oxygen flows through the manifold 44. The valves 48 associated with the lateral runners 24a and 24b are placed in the open condition whereby these runners inflate. The leg 62 is gradually and gently lifted from the patient support 22 preferably at least two inches to permit insertion of the x-ray cassette 66. The x-ray cassette 66 is removed after the x-ray has been taken and the fluid can be permitted to escape from the runners by positioning the valve 48 to the exhaust condition. The runner will collapse upon itself and the leg 62 will again return to the support surface 22.

Electric control of the valves 48 can be provided. This can be accomplished by the provision of an electric solenoid 68 for each of the valves 48 which is operable to actuate the three position valves 48 into any of the three positions. The solenoids operate to actuate the three position valves 48. Control of the solenoids 68 can conveniently be located in a control panel 70 which includes means for connection to a power source. The control panel 70 has a plurality of switch means 74–80. The switch means are operable to activate the solenoids 48 to inflate selected runners.

The switches can be connected to the runners in any desirable pattern, but it is preferable to provide a switch to operate runners which will lift a body region that must be x-rayed. Thus the single switch 74 is connected by circuit paths 82 and 84 to the respective solenoids of the runners 24a and 24b to lift the lower legs of the patient. The switch 75 is connected by paths 88 and 90 to actuate the solenoids of runners 24b and 24c to lift the thighs of the patient. The switch 76 is operable through paths 94 and 96 to actuate the solenoids of runners 24c and 24d to lift the upper chest of the patient. The switch 77 is operable through the circuit path 100 to actuate the solenoid 68 of the runner 34 to provide additional lifting force for lifting the upper chest. The switch 78 is operable through the circuit path 102 and 104 to actuate the solenoid 68 of the runners 24d and 24e to lift the head of the patient. It should be understood that the runners 30 remain in the deflated state when the head or neck is to be x-rayed so as to permit the insertion of an x-ray cassette between the runners 24d and 24e. The switch 79 is operable through a circuit path 106 to actuate the solenoid 68 of the head restraint runners 30 to secure the head in position. The switch 80 is operable through a circuit path 110 to actuate the solenoid 68 to operate a valve 112 which controls the flow of fluid into the manifold 44.

This invention can be provided in other forms without departing from the spirit or essential attributes thereof and accordingly, reference should be made to the following claims, rather than to the foregoing specification, as indicating the scope of the invention.

I claim:

1. A support for a patient to be x-rayed, said support having a plurality of spaced apart elongated inflatable runners adapted to lift portions of the patient's body, said support comprising;
   a generally flat support surface having at least one substantially U-shaped inflatable runner means, said U-shaped runner means comprising substantially parallel portions and at least one substantially perpendicular portion; and,
   connection means for placing said inflatable runner means in fluid connection with fluid supply means, whereby inflation of said runner means lifts an adjacent portion of the patient from the support surface so as to permit the insertion of an x-ray cassette beneath said portion of the patient, above the support surface, in an area bounded by said substantially U-shaped runner means.

2. The patient support of claim 1, wherein said connection means for placing said inflatable runners in fluid connection with said fluid supply means comprise at least one valve means.

3. The assembly of claim 2, wherein said connection means is selective, whereby only portions of the patient's body to be x-rayed will be lifted.

4. The assembly of claim 3, further comprising electric actuation means for actuating said valves.

5. The assembly of claim 4, further comprising electric control means adapted to control said actuation means.

6. The assembly of claim 5, wherein said electric actuation means comprise a solenoid.

7. The patient support of claim 1, wherein said connection means for placing said inflatable runners in fluid connection with said fluid supply means comprises a manifold in fluid connection with each of said runners.

8. The assembly of claim 1, wherein at least one of said runners is positioned on the support surface so as to lift the foot of the patient, and other runners are positioned so as to substantially lift the knee area, the pelvis, the upper chest, and the head of the patient when said runners are inflated.

9. The assembly of claim 1, further comprising at least two substantially parallel head restraint runners, said head restraint runners being aligned substantially perpendicular to the axis of the shoulders of the patient and spaced apart so as to restrain the head of the patient therebetween when said head restraint runners are inflated.

10. A support for a patient, comprising:
    a generally flat support surface having spaced apart, elongated concave depressions formed in the support surface, and a plurality of spaced elongated inflatable runners fixed in said concave depressions formed in the support surface; and,
    connection means for placing said inflatable runners in fluid connection with a fluid supply means, whereby inflation of said runners lifts an adjacent portion of the patient from the support surface, said runners when deflated being collapsible into said depressions, whereby no discomfort is caused to a patient supported on the support surface.

11. The patient support of claim 10, wherein said connection means for placing said inflatable runners in fluid connection with said fluid supply means comprise at least one valve means.

12. The assembly of claim 11, wherein said connection means is selective, whereby only portions of the patient's body to be x-rayed will be lifted.

13. The assembly of claim 12, further comprising electric actuation means for actuating said valves.

14. The assembly of claim 13, further comprising electric control means adapted to control said actuation means.

15. The assembly of claim 14, wherein said electric actuation means comprise a solenoid.

16. The patient support of claim 10, wherein said connection means for placing said inflatable runners in fluid connection with said fluid supply means comprises a manifold in fluid connection with each of said runners.

17. The assembly of claim 10, wherein at least one of said runners is positioned on the support surface so as to lift the foot of the patient, and other runners are positioned so as to substantially lift the knee area, the pelvis, the upper chest, and the head of the patient when said runners are inflated.

18. The assembly of claim 10, further comprising at least two substantially parallel head restraint runners, said head restraint runners being aligned substantially perpendicular to the axis of the shoulders of the patient therebetween when said head restraint runners are inflated.

19. An assembly for the recordation of an image of a patient cast by x-rays emanating from an x-ray source, said assembly comprising:

an x-ray cassette for recording said x-ray image; a generally flat patient support surface;

a plurality of lifting means disposed about the support surface at a distance from one another adapted to permit the insertion of said x-ray cassette therebetween, said lifting means comprising elongated inflatable runners, and further comprising connection means for placing said inflatable runners in fluid connection with fluid supply means, whereby inflation of said runners lifts an adjacent portion of the patient from the support surface, and permits the insertion of said x-ray cassette beneath said portion of the patient and between said adjacent runners for recordation of said x-ray image.

20. The x-ray assembly of claim 19, further comprising means for removing fluid from the runners.

21. The x-ray assembly of claim 20, wherein said connection means for placing said inflatable runners in fluid connection with said fluid supply means, and said means for removing fluid from the runners, comprise at least one valve means.

22. The x-ray assembly of claim 21, wherein said connection means for placing said inflatable runners in fluid connection with said fluid supply means comprises a manifold in fluid connection with each of said runners.

23. The x-ray assembly of claim 21, further comprising electric actuation means for actuating said valves.

24. The x-ray assembly of claim 23, further comprising electric control means adapted to control said actuation means.

25. The x-ray assembly of claim 24, wherein said electric actuation means comprise a solenoid.

26. The x-ray assembly of claim 19, wherein the runners are substantially parallel and laterally aligned on the support surface, so as to be substantially parallel with the axis of the shoulders of the patient, whereby the x-ray cassette can be positioned between adjacent runners from alongside the patient and at a plurality of locations relative to the body of the patient.

27. The x-ray assembly of claim 19, wherein at least one of said runners is positioned on the support surface so as to lift the foot of the patient, and other runners are positioned so as to substantially lift the knee area, the pelvis, the upper chest, and the head of the patient when said runners are inflated.

28. The x-ray assembly of claim 27, further comprising at least two substantially parallel head restraint runners, said head restraint runners being aligned substantially perpendicular to the axis of the shoulders of the patient and spaced apart so as to restrain the head of the patient therebetween when said head restraint runners are inflated.

29. The x-ray assembly of claim 19, wherein at least one longitudinally aligned lifting means is placed between two lateral lifting means substantially at one lateral side of said support surface, whereby a substantially U-shaped lifting means is formed.

30. The x-ray assembly of claim 19, wherein said connection means is selective, whereby only portions of the patient's body to be x-rayed will be lifted.

31. The x-ray assembly of claim 19, further comprising restraining straps fixed to the patient support.

32. The x-ray assembly of claim 31, wherein said restraining straps comprise a hook and loop fastener.

* * * * *